United States Patent [19]

Manzer

[11] 4,042,610

[45] Aug. 16, 1977

[54] PROCESS FOR PREPARING HYDROCARBYL AND SILAHYDROCARBYL TRANSITION METAL DIHYDROCARBYLAMIDES

[75] Inventor: Leo Ernest Manzer, Wilmington, Del.

[73] Assignee: E. I. Du Pont de Nemours and Company, Wilmington, Del.

[21] Appl. No.: 615,494

[22] Filed: Sept. 22, 1975

[51] Int. Cl.$^2$ .............................................. C07F 7/00
[52] U.S. Cl. ........................ 260/429.3; 260/429 R; 260/429.5; 260/438.5 R; 260/583 R
[58] Field of Search ............ 260/429 R, 429.3, 429.5, 260/438.5, 583 R

[56] References Cited

U.S. PATENT DOCUMENTS

| 3,318,932 | 5/1967 | Kornicker | 260/429 |
| 3,394,156 | 7/1968 | Kornicker | 260/429 |

FOREIGN PATENT DOCUMENTS 661,389   9/1965   Belgium

OTHER PUBLICATIONS

Chemical Abstracts, v. 72, 132915y (1970).
Bürger et al., J. Organometal Chem. 20, pp. 129–139 (1969).
Harris et al., J. C. S. Chem. Comm. p. 895 (1974).
Frohlich et al., L. Chem. 15, pp. 233–234 (1975).

*Primary Examiner*—Helen M. S. Sneed
*Attorney, Agent, or Firm*—Anthony P. Mentis

[57] ABSTRACT

A poly(dihydrocarbylamide) of a transition metal of groups IV, V or VI is reacted with a hydrocarbyllithium or a silahydrocarbyllithium in a solvent and a hydrocarbyl- or silahydrocarbyl(transition metal) dihydrocarbylamide is recovered. Exemplary is the process of dissolving vanadium tetrakis(dimethylamide) in pentane and adding trimethylsilylmethyllithium to obtain bis (trimethylsilylmethyl)vanadium bis(dimethylamide).

15 Claims, No Drawings

PROCESS FOR PREPARING HYDROCARBYL AND SILAHYDROCARBYL TRANSITION METAL DIHYDROCARBYLAMIDES

BACKGROUND OF THE INVENTION

1. Field of the Invention

This invention is a process for preparing hydrocarbyl- and silahydrocarbyl dihydrocarbylamides of selected transition metals.

2. Prior Art

Burger and Neese, J. Organometal. Chem. 20, 129 (1969) disclose tris (dialkylamino)hydrocarbyltitanium compounds obtained by a different process which reacts the bromides of titanium, i.e., $(R_2N)_3TiBr$, with organolithium and Grignard reagents.

Frohlich and Keiser, Z. Chem., 15, 30 (1975) disclose the preparation of dibenzylzirconium bis(diphenylamide) by the reaction of tetrabenzylzirconium with diphenylamine. The other product is toluene.

Belgian Patent 661,389 published Sept. 20, 1965, discloses certain organometal compounds containing titanium or zirconium, e.g. hydrocarbyltitanium dialkylamides, produced by an undisclosed process.

SUMMARY OF THE INVENTION

It has now been found that a process using readily available materials proceeds at ordinary temperatures to give good yields of products and does not involve the use of corrosive halides of the transition metals.

The process consists in reacting a poly(dihydrocarbylamide) of a transition metal of Groups IV, V or VI with a hydrocarbyllithium or a silahydrocarbyllithium in a solvent in which the reactants are soluble and the resultant lithium dihydrocarbylamide is insoluble, and isolating a hydrocarbyl- or silahydrocarbyl(transition metal) dihydrocarbylamide. The reaction can be represented:

$$M(NR_2)_x + yR'Li \rightarrow R'_yM(NR_2)_{x-y} + yLiNR_2$$

wherein:
M is a transition metal of Groups IV, V, or VI, i.e., titanium, zirconium, hafnium, vanadium, niobiume, tantalum, chromium, molybdenum, or tungsten;
R is alkyl, aryl, or aralkyl;
R' is alkyl, silaalkyl in which the silicon is bonded solely to carbon, aralkyl, or diarylmethyl;
$x$ is the valence of the metal and is at least 3 and preferably at least 4;
$y$ is 1 to 5, preferably 1 to 2; and
$x-y$ is at least 1.

The terms "aryl" and "ar" in "aralkyl" denote a radical derived from a hydrocarbon that has as its only unsaturation aromatic unsaturation in six-membered carbocylic rings by removal of a hydrogen atom from a nuclear carbon atom of an aromatic ring. Examples of aryl groups are phenyl, 1- and 2-naphthyl, o-, m-,and p-tolyl, ethylphenyl, butylphenyl, xylyl, and trimethylphenyl. Examples of aralkyl are benzyl, phenethyl, and the like.

Compounds in which one or more dihydrocarbylamino groups are bonded to a metal atom have been named in several different ways. For example, the compound of the formula $V[N(CH_3)_2]_4$, a typical starting material in the process of the invention, has been named vanadium tetrakis(dimethylamide), tetrakis(dimethylamindo)vanadium, tetrakis(dimethylamino)vanadium, and tetrakis(dimethylaminato) vanadium. The last name is the systematic name used by Chemical Abstracts. In this description the widely used "dihydrocarbylamide" nomenclature will be used, i.e., the compound $V[N(CH_3)_2]_4$ will be named vanadium tetrakis(dimethylamide), and other compounds will be named accordingly. Correspondingly, the products of the process of the invention will be named as hydrocarbyl(transition metal) dihydrocarbylamides and silahydrocarbyl(transition metal) dihydrocarbylamides.

The products of the process in which M is a transition metal of Group V or VI are new.

The only requirement appears to be that the lithium dihydrocarbylamide $LiNR_2$ be insoluble in the reaction medium and accordingly it is seen that the carbon content or structure of R and R' are not critical. The R groups on a given nitrogen atom can be the same or different but it is preferred they be the same. Examples of R are methyl, ethyl, isopropyl, butyl, t-butyl, neopentyl, hexyl, heptyl, 2-ethylhexyl, decyl, phenyl, benzyl, phenethyl, phenylbutyl, tolylmethyl, naphthyl, tolyl, xylyl, and butylphenyl. Solely because of availability, it is preferred that R contain a maximum of 10 carbons. Most preferably R is $C_1$-$C_4$ alkyl.

Because of availability, preferred R' groups are alkyl, silaalkyl, and aralkyl groups, all of at most 11 carbons, and diarylmethyl groups in which the aryl groups contain 6 to 10 carbons each. Examples of R' are methyl, ethyl, propyl, isopropyl, isobutyl, neopentyl, hexyl, isoheptyl, octyl, undecyl, 2,2,4,4-tetramethyl-3-pentyl, benzyl, p-ethylbenzyl, naphthylmethyl, neophyl, diphenylmethyl, ditolylmethyl, dixylylmethyl, trimethylsilylmethyl (2,2-dimethyl-2-silapropyl), 1-(trimethylsilyl)ethyl, 2-(trimethylsilyl)ethyl, 5-(trimethylsilyl)pentyl, 2-(triethylsilyl)ethyl, and triethylsilylmethyl. The preferred silaalkyl value of R is a trimethylsilylmethyl.

The reaction proceeds readily when $y$ is 1 or 2. However, $y$ may also be 3 or even higher, especially when $x$ is 5 or higher and under relatively extreme reaction conditions such as higher temperatures and longer times.

It is advantageous to use stoichiometric quantities of reactants, since when the reaction proceeds to completion the desired product is the only material remaining in solution. The concentration of starting material is not critical however and one can use dilute solutions or concentrated solutions up to the limits of solubility of the starting materials.

The process is carried out in a solvent in which the starting materials are soluble or have at least some solubility and the lithium amide by-product, $LiNR_2$, is essentially insoluble. The preferred solvents, because of availability, cost, and solvent properties, are hydrocarbons, especially liquid alkanes and cycloalkanes. Examples are pentane, hexane, heptane, isooctane, cyclopentane, methylcyclopentane, cyclohexane, and methylcyclohexane.

Temperature is not critical and the process usually proceeds rapidly at ordinary temperatures (20°-30° C). Lower or higher temperatures, down to the freezing point of the reaction mixture or up to the boiling point of the solvent, can be used, but usually no advantage results. Higher temperatures can sometimes be helpful in embodiments in which the transition metal amide, $M(NR_2)_x$, has relatively low solubility at ordinary temperature. However, such compounds react satisfactorily even at ordinary temperatures, although sometimes more slowly.

When the reactants are all in solution, the reaction proceeds rapidly, even at room temperature or below, and the by-product LiNR$_2$ usually precipitates in less than a minute. The mixture can be kept for from about 15 minutes to 1 hour to insure complete reaction. The lithium amide is separated by filtration or centrifugation. The products can be isolated by evaporation of the filtrate, followed by purification by conventional methods such as distillation, crystallization, and chromatography. After removal of the lithium amide, the solution of the substituted transition metal amide can be used directly without isolation in applications such as polymerization of ethylene.

The following examples illustrate the process of the invention. All preparations were carried out in an atmosphere of nitrogen since the starting materials and the products are sensitive to oxygen. In the formulas given in the various examples, Me is methyl, Et is ethyl, Bu is butyl, and Ph is phenyl.

Titanium tetrakis(dimethylamide), zirconium tetrakis(diethylamide), and hafnium tetrakis(diethylamide) were obtained commercially. Niobium tetrakis(diethylamide) and the tetrakis(dimethylamides) of vanadium, molybdenum, and zirconium were made by known procedures, involving reactions of the metal chlorides with the appropriate lithium dialkylamide. Butyllithium and t-butyllithium were obtained commercially as solutions in hexane and pentane, respectively. Other hydrocarbyl and silahydrocarbyllithiums were made by reactions of the appropriate organic halides with lithium in hexane, a known procedure.

SPECIFIC EMBODIMENTS OF THE INVENTION

In the following illustrative examples all parts are by weight and all temperatures are Centigrade unless otherwise stated.

EXAMPLE 1

Bis(trimethylsilylmethyl)vanadium bis(dimethylamide)

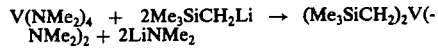

A small amount of vanadium tetrakis(dimethylamide) was dissolved in pentane, and an excess of trimethylsilylmethyllithium was added. Lithium dimethylamide precipitated. The mixture was filtered and the esr spectrum was recorded. An eight-line spectrum was observed at $g = 1.973 \pm 0.001$ with a hyperfine coupling constant to vanadium of 60.3 G. This coupling constant is midway between V(NMe$_2$)$_4$ (65.1 G) and (Me$_3$SiCH$_2$)$_4$V (55 G). This spectrum implied the existence of bis(trimethylsilylmethyl) vanadium bis(dimethylamide) in solution.

EXAMPLE 2

Bis(trimethylsilylmethyl)vanadium bis(dimethylamide)

To a stirred solution of 0.80 g of vanadium tetrakis(dimethylamide) in pentane was added a solution of 0.63 g of trimethylsilylmethyllithium in pentane. Lithium dimethylamide precipitated rapidly. The reaction mixture contained a total of about 50–100 ml of pentane. After stirring for three hours the mixture was filtered, and part of the pentane was evaporated. The solution was kept at −40° C overnight, following which the remainder of the pentane was evaporated, to give bis(trimethylsilylmethyl) vanadium bis(dimethylamide) as a dark-green oil, which was purified by distillation at 100° C under high vacuum.

EXAMPLE 3

Trimethylsilylmethyltitanium tris(dimethylamide)

To a stirred solution of 4.20 g of titanium tetrakis(dimethylamide) in about 10 ml of pentane was added a solution of 1.77 g of trimethylsilylmethyllithium in pentane. Lithium dimethylamide precipitated immediately. The mixture was stirred for 1 hour and filtered, pentane was removed from the filtrate by rotary evaporation, and the residual pale-yellow oil was distilled through a short still-head under reduced pressure, to give 0.87 g of trimethylsilylmethyltitanium tris(dimethylamide), bp 55° C (50 μ). Nmr in C$_6$D$_6$: δ (NMe) 3.07, δ (SiMe) 0.22, δ (CH$_2$) 0.35 ppm downfield from tetramethylsilane.

Nmr analysis of two fractions boiling between 46.5° and 55° C showed that they contained an additional 1.77 g of the product. The total yield of distilled material was therefore 2.64 g (53 percent). The entire yield of products can be readily separated by precision distillation.

EXAMPLE 4

Neopentylzirconium tris(dimethylamide)

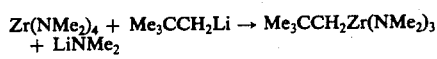

A solution of 0.50 g of neopentyllithium in hexane was added to a hot solution of zirconium tetrakis(dimethylamide) in hot hexane with stirring. Lithium dimethylamide precipitated immediately. The total amount of hexane in the reaction mixture was about 50–100 ml. The mixture was cooled and filtered, and the filtrate was evaporated to give a sticky solid. The latter was dissolved in pentane, and the solution was kept at −40° C for 2 days. During this time yellow crystals of neopentylzirconium tris(dimethylamide) separated. They were isolated by filtration and dried; yield 0.5 g. Nmr in C$_6$C$_6$: δ (NMe) 2.92, δ (CH$_2$) 0.9, δ (CMe$_3$) 1.20 ppm downfield from tetramethylsilane.

If tungsten hexakis(dimethylamide) is substituted for zirconium tetrakis(dimethylamide) in essentially the procedure of Example 4, the product will be neopentyltungsten pentakis(dimethylamide).

EXAMPLE 5

Dineopentyltitanium bis(dimethylamide)

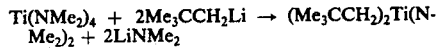

A solution of 4.87 g of neopentyllithium in pentane was added to a solution of 7.0 g of titanium tetrakis(dimethylamide) in pentane with stirring. Lithium dimethylamide precipitated rapidly. The total amount of pentane in the reaction mixture was about 50–100 ml. After being stirred for one hour the mixture was filtered, and pentane was evaporated from the filtrate to give 7.5 g (86%) of dineopentyltitanium bis(dimethylamide) as an air-sensitive yellow oil. Nmr C$_6$D$_6$: δ (NMe) 3.23, δ (CMe$_3$) 1.05 ppm downfield from tetramethylsilane.

If chromium tetrakis(dimethylamide) is substituted for titanium tetrakis(dimethylamide) in essentially the procedure of Example 5, dineopentylchromium bis(-dimethylamide) will be produced.

EXAMPLE 6

Dibutylvanadium bis(dimethylamide)

$$V(NMe_2)_4 + 2BuLi \rightarrow Bu_2V(NMe_2)_2 + 2LiNMe_2$$

To a dark-green solution of 0.048 g (0.21 mmol) of vanadium tetrakis(dimethylamide) in hexane was added from a syringe 0.26 ml of a 1.6 M solution of butyllithium (0.21 mmol) in hexane. Lithium dimethylamide precipitated rapidly. The total volume of liquid in the mixture was about 6 ml. After 15 minutes the mixture was filtered to give a clear green solution of dibutylvanadium bis(dimethylamide) in hexane.

If tantalum tetrakis(dimethylamide) is used instead of vanadium tetrakis(dimethylamide) in essentially the procedure of Example 6, the product will be dibutyltantalum bis(dimethylamide).

By essentially the method of Example 6, the process of the invention was used to prepare solutions of other substituted transition metal amides. These preparations are summarized in Table I. In each example as in Example 6, 0.21 mmol of transition metal amide was used.

added from a syringe. The suspension was stirred for five minutes and transferred through polyethylene tubing under nitrogen pressure to a dry, oxygen-free, ordinary-steel autoclave equipped with a stirrer. The stirrer was run at 1000 rpm right after the addition and during the polymerization. The autoclave was heaed to 60° C, the nitrogen was replaced by ethylene at 100 psi, and the system was heated at 60° C and 100 psi, ethylene being added to maintain this pressure, until 90 g of ethylene has been added in addition to the amount used initially to reach 100 psi (45 g). The aim was to consume 90 g of ethylene and to form an approximately 185/90 (67/33) clay/polyethylene composition. The time required was 1.13 hr. The autoclave was immediately vented to atmosphereic pressure and cooled, and the solid composition was separated by filtration and air-dried to give 267.1 g of powder that passed a 20 mesh screen.

A portion of the powder was added to a $CHBr_3:CCl_4$ mixture (1:1 by weight); all the powder floated, indicating that no unattached clay particles were present, i.e., that essentially all the clay particles had been coated with polyethylene. In a similar test with $CCl_4$:n-$C_3H_7OH$ (3:2 by volume), all the powder sank, indicating that essentially no clay-free polyethylene was present. The product gave 57.18% ash on combustion, corresponding to a clay content of 66.5%. The inherent

TABLE I
PREPARATION OF SOLUTIONS OF HYDROCARBYL(TRANSITION METAL) DIHYDROCARBYLAMIDES

| Example | Transition Metal Amide | Mmol Hydrocarbyllithium | Solvent | Color of final solution | Product |
|---|---|---|---|---|---|
| 7 | $Ti(NMe_2)_4$ | 0.42 $Me_3CH_2Li$ | Pentane | Yellow | $(Me_3CCH_2)_2Ti(NMe_2)_2$ |
| 8 | $Zr(NMe_2)_4$ | 0.21 $Me_3CH_2Li$ | " | Pale Yellow | $Me_3CCH_2Zr(NMe_2)_3$ |
| 9 | $Zr(NMe_2)_4$ | 0.42 $Me_3CH_2Li$ | " | Pale Yellow | $(Me_3CCH_2)_2Zr(NMe_2)_2$ |
| 10 | $V(NMe_2)_4$ | 0.42 $Me_3CH_2Li$ | " | Yellow-green | $(Me_3CCH_2)_2V(NMe_2)_2$ |
| 11 | $Nb(NEt_2)_4$ | 0.42 $Me_3CH_2Li$ | " | Brown | $(Me_3CCH_2)_2Nb(NEt_2)_2$ |
| 12 | $Mo(NMe_2)_4$ | 0.42 $Me_3CH_2Li$ | " | Purple | $(Me_3CCH_2)_2Mo(NMe_2)_2$ |
| 13 | $Zr(NEt_2)_4$ | 0.42 BuLi | Hexane | Pale yellow | $Bu_2Zr(NEt_2)_2$ |
| 14 | $Ti(NMe_2)_4$ | 0.42 BuLi | Pentane/hexane | Orange | $Bu_2Ti(NMe_2)_2$ |
| 15 | $Hf(NEt_2)_4$ | 0.42 BuLi | Hexane | Pale yellow | $Bu_2Hf(NEt_2)_2$ |
| 16 | $Ti(NMe_2)_4$ | 0.42 t-BuLi | Pentane | Yellow | $(t-Bu)_2Ti(NMe_2)_2$ |
| 17 | $Ti(NMe_2)_4$ | 0.42 $PhCMe_2CH_2Li$ | Hexane | Yellow | $(PhCMe_2CH_2)_2Ti(NMe_2)_2$ |

Because of their sensitivity to oxygen, the products made by the process of the invention are useful for removing small amounts of oxygen from gases and mixtures of gases. For this purpose a given product can be used in a solution in an inert solvent. In addition, a product can be deposited on an inert support from a solution in an inert solvent. After removal of traces of solvent by evaportion, the product-coated support can be used for trapping oxygen.

In addition, as shown in the following example, the products made by the process of the invention are useful as components of catalyst systems for the polymerization of ethylene on the surface of clay to give polyethylene/clay composites.

EXAMPLE A

Up to the start of the polymerization, all operations were carried out under dry nitrogen. Two liters of reagent-grade cyclohexane were passed through a 3-inch bed of Woelm acid alumina into a 5-l. roundbottom flask fitted with a blender in its base. Stirring was started and 7.5 mmol of triisobutylaluminum was added from a syringe, followed after 10-15 seconds by 185 g of "Harwick" GK kaolinite clay that had been dried at 250°14 275° C for 16 hours in a stream of nitrogen and cooled under nitrogen. After stirring for one minute, a solution of 0.2 mmol (53 mg) of trimethylsilylmethyltitanium tris(dimethylamide) in 6 ml of toluene was viscosity of the polyethylene was 16.66 (0.05 w/v % in 1,2,4-trichlorobenzene).

Molded bars were made by hot-compression molding and were tested by standard ASTM methods. They had the following properties:

Tensile strength, $T_{max}$: 2712, 2740 psi
Tensile modulus, $M_i$: 575, 708 kpsi
Elongation at break, $E_b$: 252%, 291%
25° C Gardner impact strength : 240 in lb
0° F Izod impact strength: 3.01, 3.47 ft lb/in.

By essentially the method of Example A, with triethylaluminum in place of triisobutylaluminum, polyethylene/clay composites were also prepared by using, in place of trimethylsilylmethyltitanium tris(dimethylamide), the products of Examples 2, 4, 5, 7-10, and 12-17.

The properties and uses of polyethylene/clay composites of the type described above are described further in assignee's copending application Ser. No. 573,598, filed Apr. 30, 1975, now abandoned in the name of Edward G. Howard, Jr. and in German Patent Publication P 24 59 118. For example, the polyethylene/clay composites can be used in a wide variety of applications. They can be used as house sidings, wall panels, containers, dishes, instrument housings, insulators, and the like.

I claim:

1. The process of reacting a poly(dihydrocarbylamide) of a transition metal having the formula $M(NR_2)_x$ with $yR'Li$ in a solvent in which both reactants are soluble to produce a compound of the formula $R'_y M(NR_2)_{x-y}$ and a by-product of the formula $LiNR_2$ which in insoluble in the solvent wherein M is titanium, zirconium, hafnium, vanadium, niobium, tantalum, chromium, molybdenum or tungsten;

R is alkyl, aryl or aralkyl;

R' is alkyl, silaalkyl in which the silicon is bonded solely to carbon, aralkyl or diarylmethyl;

$x$ is the valence of the metal and is at least 3;

$y$ is 1 to 5; and $x$-$y$ is at least 1.

2. The process of claim 1 in which the solvent is a liquid alkane or liquid cycloalkane.

3. The process of claim 2 in which the solvent is pentane.

4. The process of claim 1 in which R has a maximum of 10 carbons.

5. The process of claim 1 in which R is alkyl of up to 4 carbons.

6. The process of claim 1 in which R' has a maximum of 11 carbons and in which the aryl groups contain 6–10 carbons each.

7. The process of claim 1 in which the transition metal reactant is vanadium tetrakis(dimethylamide).

8. The process of claim 1 in which the transition metal reactant is titanium tetrakis(dimethylamide).

9. The process of claim 1 in which the transition metal reactant is tantalum tetrakis(dimethylamide).

10. The process of claim 1 in which the transition metal reactant is zirconium tetrakis(dimethylamide).

11. The process of claim 1 in which the transition metal reactant is chromium tetrakis(dimethylamide).

12. The process of claim 1 in which the transition metal reactant is molybdenum tetrakis(dimethylamide).

13. The process of claim 1 in which the transition metal reactant is niobium tetrakis(diethylamide).

14. The process of claim 1 in which the transition metal reactant is hafnium tetrakis(diethylamide).

15. The process of claim 1 in which the transition metal reactant is tungsten hexakis(dimethylamide).

* * * * *

UNITED STATES PATENT OFFICE
CERTIFICATE OF CORRECTION

PATENT NO. : 4,042,610
DATED : August 16, 1977
INVENTOR(S) : Leo Ernest Manzer

It is certified that error appears in the above–identified patent and that said Letters Patent are hereby corrected as shown below:

Column 7, line 9, "which in" should be --which is--.

Signed and Sealed this

Twenty-first Day of February 1978

[SEAL]

Attest:

RUTH C. MASON
Attesting Officer

LUTRELLE F. PARKER
Acting Commissioner of Patents and Trademarks